US00PP09742P

United States Patent [19]

Dümmen

[11] Patent Number: Plant 9,742

[45] Date of Patent: Dec. 10, 1996

[54] NEW GUINEA IMPATIENS PLANT NAMED 'HWD BOURREE'

[75] Inventor: Günter Dümmen, Rheinberg-Eversael, Germany

[73] Assignee: Dümmen Jungpflanzenkulturen, Rheinberg-Eversael, Germany

[21] Appl. No.: 516,464

[22] Filed: Aug. 17, 1995

[51] Int. Cl.[6] ..... A01H 5/0

[52] U.S. Cl. ..... Plt./87.6

[58] Field of Search ..... Plt./87.6

*Primary Examiner*—James R. Feyrer

*Attorney, Agent, or Firm*—Proprietary Rights International

[57] ABSTRACT

A new and distinct cultivar of New Guinea Impatiens plant named HWD Bourree, characterized by its large orange iridescent flowers; compact and freely branching growth habit; moderate vigor; and medium green and glossy non-variegated foliage.

1 Drawing Sheet

The present invention relates to a new and distinct cultivar of New Guinea Impatiens plant, botanically known as *Impatiens hawkeri,* known as the variety Duebur, and hereinafter referred to by the cultivar name HWD Bourree.

The new cultivar is a product of a planned breeding program conducted by the inventor in Rheinberg, Germany. The objective of the breeding program was to develop a new orange-flowered variety that was freely branching.

The new cultivar originated from a cross made by the inventor of the proprietary selection 88-100-4 as the male or pollen parent with the proprietary selection 88-103-8 as the female or seed parent.

The cultivar HWD Bouree was discovered and selected by the inventor as a flowering plant within the progeny of the stated cross in a controlled environment in Rheinberg, Germany. Asexual reproduction of the new cultivar by terminal cuttings taken at Rheinberg, Germany, has shown that the unique features of this new Impatiens are stabilized and reproduced true to type in successive generations of asexual reproduction.

The following traits have been repeatedly observed and are determined to be the unique characteristics of HWD Bourree. These characteristics in combination distinguish HWD Bourree as a new and distinct cultivar:

1. Large orange flowers.
2. Compact growth habit.
3. Moderately vigorous.
4. Freely branching plant habit.
5. Medium green and glossy non-variegated foliage.

In comparison to the parent selection 88-100-4, the new Impatiens is more freely branching and flowers are not as bright orange in color. In comparison to the parent selection 88-103-8, the new Impatiens has larger flowers that are not as bright orange in color.

The new Impatiens is most similar to the patented cultivars Selenia (U.S. Plant Pat. No. 6,731) and Antigua (U.S. Plant Pat. No. 8,283). However, the new Impatiens differs from these cultivars in the following characteristics: the new Impatiens is more compact than the cultivar Antigua; foliage color of the new Impatiens is a different color of green than the cultivars Selenia and Antigua; the new Impatiens has a lighter flower color than the cultivar Antigua; flower color of the new Impatiens is more orange than the cultivar Selenia; and moreover, the new Impatiens has larger flowers than the cultivars Selenia and Antigua.

The accompanying colored photograph illustrates the overall appearance of the new cultivar, showing the colors as true as it is reasonably possible to obtain in colored reproductions of this type. Flower color appears slightly darker in the photograph due to light reflectance. The photograph comprises a top perspective view of a typical potted plant of HWD Bourree with one plant in a 15-cm container.

The cultivar HWD Bourree has not been observed under all possible environmental conditions. The phenotype may vary somehwat with variations in environment such as temperature and light intensity, without, however, any variance in genotype. The following obervations, measurements and comparisons describe plants grown in Rheinberg, Germany, under commercial practice in a glass-covered greenhouse with day temperatures of 28° C. and night temperatures of 20° to 22° C. and light levels of 30,000 to 40,000 lux. In the following description, color references are made to the Royal Horticultural Society Colour Chart where general terms of ordinary dictionary significance are used.

Classification:

*Botanical.*—*Impatiens hawkeri.*

*Commercial.*—New Guinea Impatiens.

*Cultivar.*—'HWD Bourree'.

Parentage:

*Male parent.*—Proprietary selection 88-100-4.

*Female parent.*—Proprietary selection 88-103-8.

Propagation:

*Type cutting.*—Terminal cuttings.

*Time to initiate roots.*—Summer: 27° C., 21 days; winter 20° C., 28 days.

Plant Description

General appearance: Rounded; freely branching and compact growth habit; upright and spreading; moderately vigorous; suitable for 10 to 16-cm pots.

Plant height: 14 to 16 cm from soil level to top of plant plane.

Foliage description:

*Shape.*—Elliptic with acuminate tip and attenuate base.

*Size.*—Length: 11 cm. Width: 4 cm.

*Texture.*—Smooth, glossy, and glabrous.

*Margin.*—Finely serrated, ciliate.

*Petiole length.*—1 cm.

*Color.*—Young foliage, upper surface: 137A. Young foliage, under surface: 148A. Mature foliage, upper surface: 137A. Mature foliage, under surface: 148A. Veins, upper surface: 59B. Veins, under surface: 59B. Petiole: 59B.

Stem description:

*Internode length.*—3 cm.

*Stem color.*—59A.

Flowering Description

Flowering habit: Freely flowering.

Natural flowering season: Year-round. Under summer conditions, plants flower 6 to 7 weeks after planting; under winter conditions, plants flower 9 to 11 weeks after planting.

Flowers borne: Flower buds develop in apical leaf axils. Open flowers are displayed above the foliage.

Quantity of inflorescences: Very floriferous; usually 8 to 10 buds and flowers per axil; usually 15 to 20 open flowers per plant open at one time.

Flower longevity on plant: From opening, flowers will last 7 to 12 days.

Flower diameter: 7 cm.

Flower depth (height): 1.5 to 2.5 cm.

Petals:

*Shape.*—Cordate.

*Quantity, arrangement.*—5 petals overlapping.

*Aspect.*—Flat.

*Size.*—Length: 3.5 cm. Width: 4 to 6 cm.

*Texture.*—Smooth, satiny, and glabrous.

*Margin.*—Entire.

*Color.*—When opening: 33A. Upper surface: Brighter than 33A, iridescent. Under surface: 40B. Fading to: Petal color does not fade, but eye becomes 55C with age.

Peduncle:

*Angle.*—Erect.

*Length.*—5.5 cm.

*Color.*—46A.

Flower bud:

*Shape.*—Ovoid with spur.

*Length.*—1.8 cm.

*Diameter.*—7 mm.

*Color.*—42A.

Spur:

*Shape.*—Needle-shaped, curved at end.

*Color.*—46A.

Sepals:

*Arrangement.*—Opposite.

*Quantity.*—2.

*Shape.*—Ensiform with acuminate tip.

*Texture.*—Smooth and glabrous.

*Margin.*—Entire.

Color.—46A fading to 144B near tip.

Reproductive organs:

*Androecium.*—Stamen number: 5. Anther color: Base, 42B, top, 11C. Pollen color: 11D.

*Gynoecium.*—Stigma color: 144D. Ovary color: 144A/149A. Ovary size: 1 to 2 mm.

*Seed.*—Seed development is rarely observed.

Disease resistance: No fungal, bacterial nor viral problems observed.

It is claimed:

1. A new and distinct cultivar of New Guinea Impatiens plant named HWD Bourree, as illustrated and described.

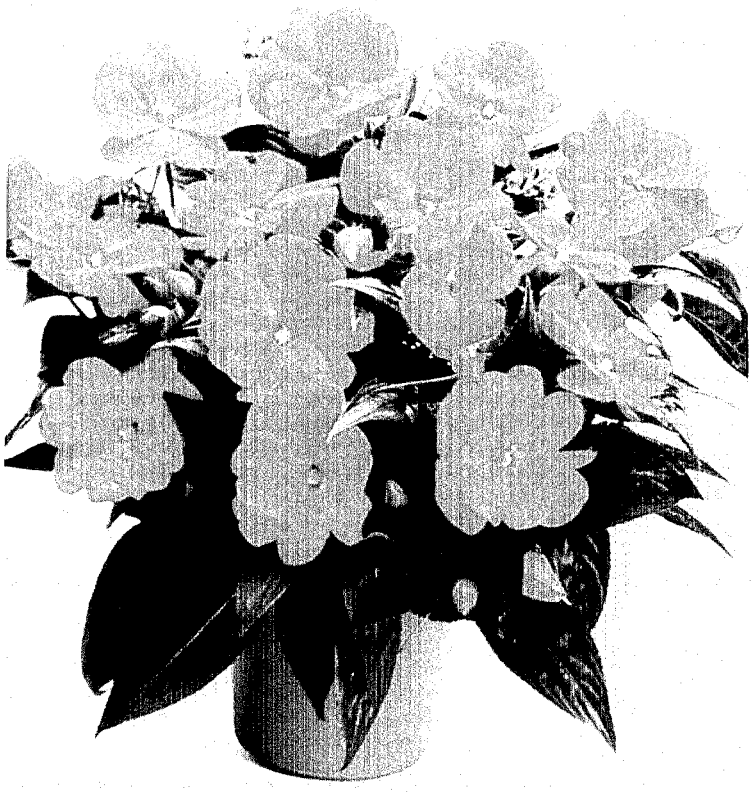

* * * * *